United States Patent [19]
Boyle et al.

[11] Patent Number: 5,591,198
[45] Date of Patent: Jan. 7, 1997

[54] MULTIPLE SINUSOIDAL WAVE CONFIGURATION STENT

[75] Inventors: William J. Boyle, Carlsbad; Rosalinda A. Wong, San Diego; James M. Shy, Chula Vista, all of Calif.

[73] Assignee: Medtronic, Inc., Minneapolis, Minn.

[21] Appl. No.: 429,975

[22] Filed: Apr. 27, 1995

[51] Int. Cl.$^6$ ................................................. A61M 29/00
[52] U.S. Cl. .................. 606/198; 623/1; 623/12; 606/108
[58] Field of Search ................. 606/108, 191, 606/194, 195, 198, 200; 623/1, 12

[56] References Cited

U.S. PATENT DOCUMENTS

| | | |
|---|---|---|
| 4,649,922 | 3/1987 | Wiktor . |
| 4,886,062 | 12/1989 | Witkor . |
| 4,969,458 | 11/1990 | Witkor . |
| 5,019,090 | 5/1991 | Pinchuk . |
| 5,116,365 | 5/1992 | Hillstead . |
| 5,133,732 | 6/1992 | Wiktor . |
| 5,330,500 | 7/1994 | Song ............................................ 623/1 |
| 5,354,308 | 10/1994 | Simon et al. ............................. 606/198 |
| 5,370,683 | 12/1994 | Fontaine .................................. 606/198 |
| 5,383,892 | 1/1995 | Cardon et al. ........................... 606/198 |

*Primary Examiner*—Michael Powell Buiz
*Assistant Examiner*—William Lewis
*Attorney, Agent, or Firm*—Dianne M. F. Plunkett; Harold R. Patton

[57] ABSTRACT

The present invention is accomplished by providing a method and apparatus for a radially expandable stent for implantation within a body vessel, comprising a large wire formed winding segment and 2 small wire formed winding segments. The large wire formed winding segment has a hollow cylindrical shape including a preformed pattern such as a sinusoidal wave form being wound into a continuous helix the length of the stent. The second and third wire formed winding segments have a hollow cylindrical shape including a preformed pattern such as a sinusoidal wave form wound into a continuous helix. The uniform pattern of the first, second and third wire segments permit uniform expansion of the stent. The second and third winding segments have more wire per unit surface area than the first winding segment. The second winding segment proximal end is attached to the distal end of the second winding segment to form a ring. The second winding segment is attached to the proximal end of the first winding segment. The third winding segment proximal end is attached to the distal end of the third winding segment to form a ring. The third winding segment is attached to the distal end of the first winding segment. The first, second and third winding segments may be formed of a unitary wire or may be formed from two or more wires. A member within the first, second and third winding segments to expand the first, second and third winding segments is included.

21 Claims, 2 Drawing Sheets

MULTIPLE SINUSOIDAL WAVE CONFIGURATION STENT

FIELD OF THE INVENTION

The present invention relates to intravascular stent implants for maintaining vascular patency in humans and animals and more particularly to a stent in the form of a tight wave segment at the proximal and distal ends of the stent. The tight wave segment being formed of small waves in both length and amplitude.

BACKGROUND OF THE INVENTION

Percutaneous transluminal coronary angioplasty (PTCA) is used to reduce arterial build-up of cholesterol fats or atherosclerotic plaque. Typically a guidewire is steered through the vascular system to the site of therapy. A guiding catheter, for example, can then be advanced over the guidewire and a balloon catheter advanced within the guiding catheter over the guidewire. The balloon at the distal end of the catheter is inflated causing the site of the stenosis to widen. The dilatation of the occlusion, however, can form flaps, fissures and dissections which threaten re-closure of the dilated vessel or even perforations in the vessel wall. Implantation of a metal stent can provide support for such flaps and dissections and thereby prevent reclosure of the vessel or provide a patch repair for a perforated vessel wall until corrective surgery can be performed. Reducing the possibility of restenosis after angioplasty reduces the likelihood that a secondary angioplasty procedure or a surgical bypass operation will be necessary.

An implanted prosthesis such as a stent can preclude additional procedures and maintain vascular patency by mechanically supporting dilated vessels to prevent vessel collapse. Stents can also be used to repair aneurysms, to support artificial vessels as liners of vessels or to repair dissections. Stents are suited to the treatment of any body lumen, including the vas deferens, ducts of the gallbladder, prostate gland, trachea, bronchus and liver or any other lumen of the body. The invention applies to acute and chronic closure or reclosure of body lumens.

A stent is a cylindrically shaped wire formed device intended to act as a permanent prosthesis. It has a plurality of metal elements joined to permit flexing of the cylindrical body along its longitudinal axis thereby conforming to a curved body lumen. A stent can be implanted during a single angioplasty procedure by using a balloon catheter bearing a stent which has been crimped onto the balloon. Stents radially expand as the balloon is inflated, forcing the stent into contact with the body lumen thereby forming a supporting relationship with the vessel walls. Deployment is effected after the stent has been introduced percutaneously, transported transluminally and positioned at a desired location by means of the balloon catheter.

Various shapes of stents are known in the art. U.S. Pat. No. 4,649,922 to Wiktor for "Catheter Arrangement Having A Variable Diameter Tip and Spring Prothesis" discloses a linearly expandable spring-like stent. U.S. Pat. No. 4,886,062 to Wiktor for "Intravascular Radially Expandable Stent and Method of Implant" discloses a two-dimensional zig-zag form, typically a sinusoidal form. U.S. Pat. No. 4,969,458 to Wiktor for "Intracoronary Stent and Method of Simultaneous Angioplasty and Stent Implant" discloses a stent wire coiled into a limited number of turns wound in one direction then reversed and wound in the opposite direction with the same number of turns, then reversed again and so on until a desired length is obtained. U.S. Pat. No. 5,019,090 to Pinchuk for "Radially Expandable Endoprosthesis and the Like" discloses a plurality of adjacent generally circumferential sections that are substantially axially positioned with respect to each other. At least one of the generally circumferential sections has a generally circumferentially disposed expandable segment that imparts circumferential and radial expandability to the stent. U.S. Pat. No. 5, 116,365 to Hillstead for a "Stent Apparatus and Method for Making" discloses a stent constructed from two elongated wires which are each bent into a series of tight bends. The two wires are permanently adhered at a first interconnection junction. The two wires are then wrapped around a mandrel repeatedly forming two opposing series of interconnections. U.S. Pat. No. 5,133,732 to Wiktor for "Intravascular Stent" discloses a stent body coiled from a generally continuous wire with a deformable zigzag structure with a means for preventing the stent body from stretching along its longitudinal axis.

SUMMARY OF THE INVENTION

It is an object of the invention to provide greater metal mass at the ends of the stent to achieve better visualization under fluoroscopy thereby allowing better stent positioning capability.

The present invention is accomplished by providing a method and apparatus for a radially expandable stent for implantation within a body vessel, comprising a large wire formed winding segment and 2 small wire formed winding segments. The large wire formed winding segment has a hollow cylindrical shape including a preformed pattern such as a sinusoidal wave form being wound into a continuous helix the length of the stent. The second and third wire formed winding segments have a hollow cylindrical shape including a preformed pattern such as a sinusoidal wave form wound into a continuous helix. The uniform pattern of the first, second and third wire segments permit uniform expansion of the stent. The second and third winding segments have more wire per unit surface area than the first winding segment. The second winding segment proximal end is attached to the distal end of the second winding segment to form a ring. The second winding segment is attached to the proximal end of the first winding segment. The third winding segment proximal end is attached to the distal end of the third winding segment to form a ring. The third winding segment is attached to the distal end of the first winding segment. The first, second and third winding segments may be formed of a unitary wire or may be formed from two or more wires. A means within the first, second and third winding segments to expand the first, second and third winding segments is included.

DETAILED DESCRIPTION OF THE PREFERRED EMBODIMENTS

Figure 1:
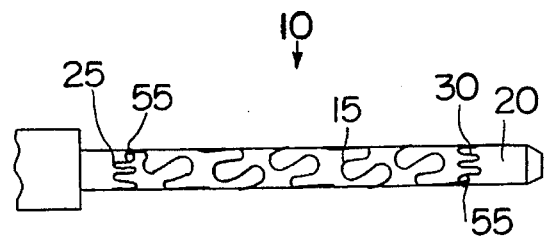
FIG. 1 is a side elevation view of a preferred embodiment of a stent being wound on a mandrel according to this invention.

Referring to FIG. 1, stent 10 is formed by winding a first wire segment around a mandrel 20 into a preformed pattern the length of the stent such as a large sinusoidal wave form 15 helix. The preferred form of the sinusoidal wave would have a length of 0.150 inches to 0.090 inches and a wave amplitude of between 0.080 inches and 0.050 inches. Any wave length and amplitude combination that would provide adequate vessel 50 hoop strength and vessel 50 coverage is appropriate. Those skilled in the art would recognize that patterns other than a sinusoidal wave pattern would be acceptable as long as the stent 10 expanded evenly and permitted the balloon 35 to expand evenly. The outer diameter of the mandrel 20 can range from 0.175 inches to 0.065 inches depending on the balloon 35 size to be used and most preferably a 0.100 inch outer diameter mandrel 20 which is suitable for the most common balloon 35 sizes. A second wire segment is then wound around the mandrel 20 into a first small preformed wave form 25 pattern. A third wire segment is then wound around the mandrel 20 into a second small preformed wave form 30 pattern. The proximal end of the large wave form 15 is attached to the first small wave form 25. The distal end of the large wave form 15 is attached to the third small wave form 30. The proximal end and distal end of the first small wave form 25 are attached to each other forming a ring. The proximal and distal ends of the second small wave form 30 are attached to each other forming a ring. The means of attachment include looping 55 the end segments together, twisting, biocompatible adhesive, welding or stamping. Those skilled in the art would recognize that the first second and third wire segments could be formed from a unitary wire or from two or more wires.

The first and second small wave forms 25 and 30 may have a preformed pattern such as a sinusoidal wave form wound into a continuous helix. The preferred length of the waves in the small wave forms 25 and 30 is 0.050 inches. The preferred amplitude of the waves in the small wave forms 25 and 30 is 0.030 inches. This allows the stent to be crimped onto a balloon such that the waves do not overlap. Those skilled in the art would recognize that other combinations of wave lengths and amplitudes are possible depending upon the circumferential dimension of the wrapped balloon 35 which will receive the stent 10. The object is to form the tightest and most densely crimped first and second small wave form 25 and 30 without overlapping the wire waves.

Those skilled in the art would recognize that patterns other than the sinusoidal pattern would be acceptable for the first and second small wave forms 25 and 30 as long as the pattern expanded evenly and permitted the balloon 35 to expand evenly. The first and second small wave forms 25 and 30 at the proximal and distal ends of the stent are formed of smaller waves in both length and amplitude than the wave length and amplitude of the large wave form 15. The ring of small wave forms 25 and 30 extend around the circumference of the mandrel 20. The advantage of the tight first and second small wave forms 25 and 30 is that it provides greater metal mass at the ends of the stent which achieves better visualization under fluoroscopy thereby allowing better stent positioning capability. More wire per unit surface area at the ends of the stent 10 also provides greater radial (hoop) strength at the proximal and distal ends of the stent.

The stent 10 is further processed onto a 0.080 inch diameter forming mandrel 20 then onto a 0.065 inch diameter forming mandrel 20. The forming mandrel 20 sequence allows a gradual reduction in the stent 10 outer diameter. Although it is possible to go directly from a 0.150 inch outer diameter to a 0.065 inch outer diameter forming mandrel 20 and make an acceptable stent, it is more difficult to do so.

Figure 2:
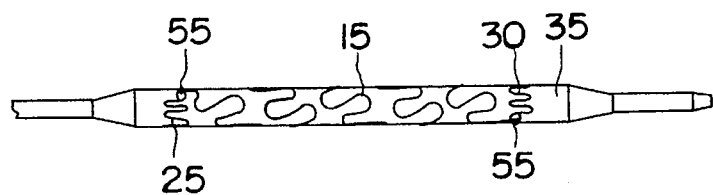
FIG. 2 is a side elevation view showing an overall view of a stent prosthesis fitted over a deflated balloon.
Figure 3:
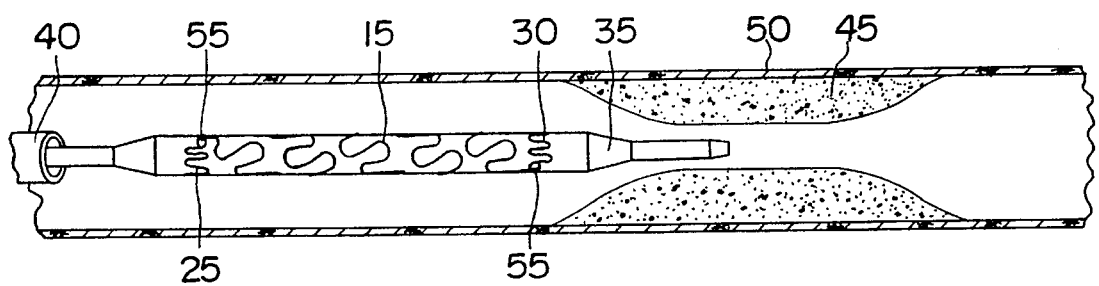
FIG. 3 is the balloon and stent assembly advanced within a vessel, entering a partial occlusion.
Figure 4:
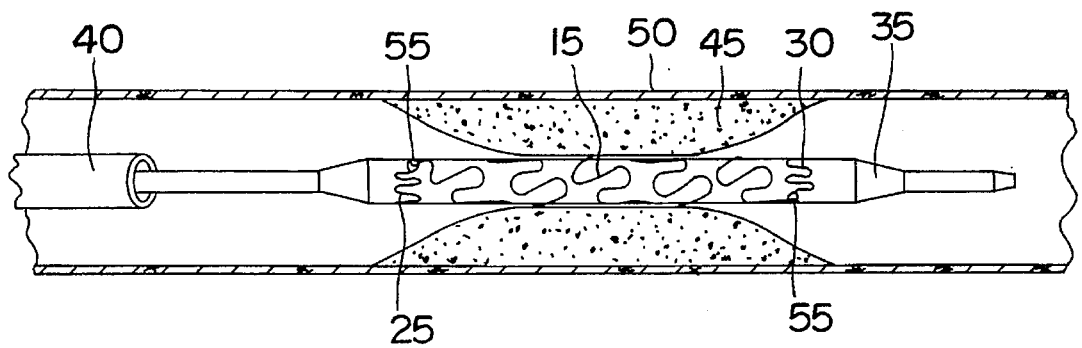
FIG. 4 is similar to FIG. 3 showing the balloon and stent assembly inside a partially occluded vessel.
Figure 5:
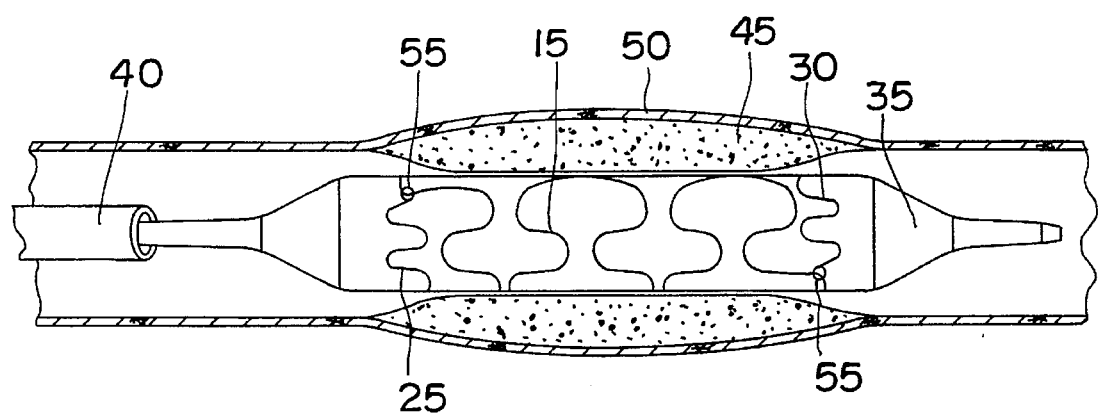
FIG. 5 is similar to FIG. 4 with the balloon inflated and the stent radially expanded illustrating an angioplasty procedure with a simultaneous deployment and implantation of a permanent prosthesis stent.
Figure 6:
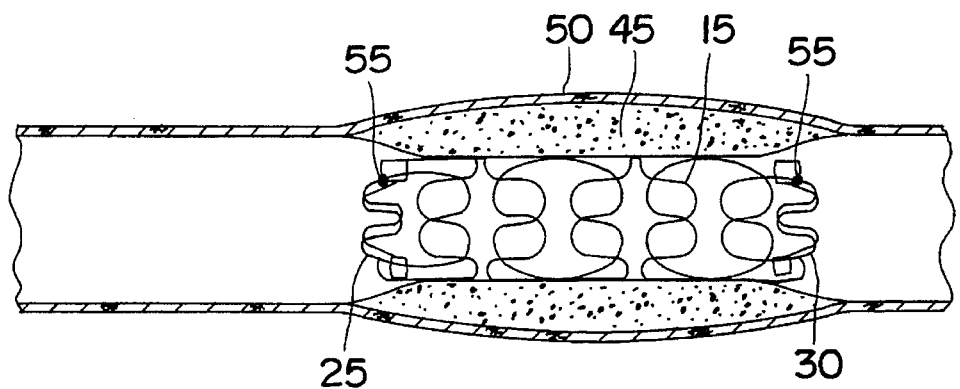
FIG. 6 is a view similar to FIG. 5 showing the plaque compressed and the prosthesis stent implanted and retained after removal of the balloon.

The stent 10 is removed from the mandrel 20 and placed over a suitable expandable diameter device such as an inflatable balloon 35 typically used for angioplasty procedures. A stent can be implanted during a single angioplasty procedure by using a balloon catheter bearing a stent 10 which has been crimped with a suitable crimping tool (not shown) onto the balloon 35 as shown in FIG. 2. Manually squeezing the stent 10 over the balloon 35 is also acceptable. FIG. 3 shows how the balloon 35 and stent 10 assembly emanate from a guiding catheter 40 inside vessel 50 and are advanced toward a partial occlusion 45. Once the balloon 35 is lodged in the stenosis 45 as seen in FIG. 4, the balloon 35 can be inflated as in FIG. 5 using standard angioplasty procedures and techniques. Stent 10 is thereby radially expanded as the balloon 35 is inflated, causing the stent 10 to contact the body lumen thereby forming a supporting relationship with the vessel walls as seen in FIG. 6. As balloon 35 expands, so does stent 10. The expanding balloon 35 together with the stent 10 compresses the plaque 45 in the stenosis and prevents possible reocclusion. When the angioplasty procedure is completed, balloon 35 is deflated and withdrawn leaving stent 10 firmly implanted within vessel 50. Previously occluded vessel 50 is recannalized and patency is restored. FIG. 6 shows stent 10 firmly implanted and imbedded in compressed plaque 45, providing both adequate support as well as a smooth lumen void of protrusions. Any protrusions are conducive to turbulent blood flow and potential formation of thrombosis.

The stent 10 can have a diameter of 0.001 inches to 0.015 inches. A typical stent 10 ranges from 5 mm to 50 mm in length. The stent 10 can be made of a low memory level metal such as tantalum, the preferred embodiment. Other acceptable materials include, stainless steel, titanium ASTM F63–83 Grade 1 or high carat gold K 19–22. A copper alloy, typically 110, when properly coated with polyester or Teflon ® can also be used. Titanium and gold are biologically compatible and inert requiring no special coating or other treatment.

A problem with solid tantalum stents is that they may glow too brightly under fluoroscopy making it difficult to see the stent edges. One solution is to use clad materials. Clad materials are composed of one alloy on the outside and another alloy on the inside. With this design, a radiopaque material such as tantalum could be used on the inside. A higher strength material, such as stainless steel or a superalloy such as MP-35N, could be used on the outside thereby reducing the brightness of the tantalum. Applicant tested using three 0.005 inch wire diameter stent samples. The first sample comprised a tantalum control sample with more than 99.7 weight % tantalum. The second sample comprised a stainless steel 316 clad alloy with 25% tantalum by volume. The third sample comprised an MP-35N clad alloy with 33% tantalum by volume. Each of the three wire samples were wrapped around a plastic test tube approximately ½ inches in diameter. An 80 KV heart grid simulating the density of a human thorax was placed between the fluoroscopy energy source and the wire samples. The third sample proved the most suitable given that the first sample was too bright with less well defined edges and the second sample was somewhat dim.

As shown in FIG. 2, stent 10 is centrally located and positioned with respect to the length of balloon 35. The stent 10 turns are evenly spaced so that when the stent 10 is expanded as shown in FIG. 5, the stent 10 will provide even support inside vessel 50, and resist external loading.

The preceding specific embodiments are illustrative of the practice of the invention. It is to be understood, however, that other expedients known to those skilled in the art or disclosed herein, may be employed without departing from the spirit of the invention or the scope of the appended claims.

| No. | Component |
|-----|-----------|
| 10 | Stent |
| 15 | Large Wave Form (First Wire Segment) |
| 20 | Mandrel |
| 25 | First Small Wave Form (Second Wire Segment) |
| 30 | Second Small Wave Form (Third Wire Segment) |
| 35 | Balloon |
| 40 | Guide Catheter |
| 45 | Plaque |
| 50 | Vessel |
| 55 | Loop |

What is claimed is:

1. A radially expandable stent for implantation within a body vessel, comprising:

a first wire formed winding having a hollow cylindrical shape defining a lumen, the first winding including a preformed sinusoidal wave pattern wound into a continuous helix the length of the stent which permits even expansion of the first winding, the first winding having a proximal end and a distal end, each wave having a wave length and a wave amplitude such that the wave length and wave amplitude ratio results in unaligned wave apexes in adjoining waves of the first wire foraged winding;

a second wire formed winding having a hollow cylindrical shape defining a lumen, the second winding including a preformed sinusoidal wave pattern wound into a continuous helix which permits even expansion of the second winding, the second winding having a wave length which is less than the wave length of the first winding such that the second winding has more wire per unit surface area than the first winding, the second winding having a proximal end and a distal end attached to each other to form a ring, the second winding being attached to the proximal end of the first winding;

a third wire formed winding having a hollow cylindrical shape defining a lumen, the third winding including a preformed sinusoidal wave pattern wound into a continuous helix which permits even expansion of the third winding, the third winding having a wave length which is less than the wave length of the first winding such that the third winding has more wire per unit surface area than the first winding, the third winding having a proximal end and a distal end attached to each other to form a ring, the third winding being attached to the distal end of the first winding; and a means extending longitudinally throughout the first, second and third winding lumens to expand the first, second and third windings.

2. The stent according to claim 1 wherein the first, second and third windings are formed of a biocompatible low memory level metal.

3. The stent according to claim 1 wherein the first, second and third windings are formed of a biocompatible clad alloy having a radiopaque material covered with a higher strength material.

4. The stent according to claim 1 wherein the first, second and third windings are formed of MP-35N with at least 33% tantalum by volume.

5. The stent according to claim 1 wherein the first, second and third windings are formed of a stainless steel alloy 316 with greater than 25% tantalum by volume.

6. The stent according to claim 1 wherein the means for expanding the first, second and third windings is an expandable balloon extending longitudinally within the first, second and third winding.

7. The stent according to claim 1 wherein the first winding has a sinusoidal wave form pattern wound into a continuous helix, the first winding having a uniform wave length and amplitude.

8. The stent according to claim 7 wherein the first winding has a wave length of about 0.150 inches to about 0.090 inches.

9. The stent according to claim 7 wherein the first winding has a wave amplitude of about 0.080 inches to about 0.050 inches.

10. The stent according to claim 1 wherein the second winding has a wave amplitude smaller than the wave amplitude of the first winding.

11. The stent according to claim 10 wherein the second winding has a wave length of about 0.050.

12. The stent according to claim 10 wherein the second winding has a wave amplitude of about 0.030 inches.

13. The stent according to claim 1 wherein the third winding has a wave amplitude smaller than the wave amplitude of the first winding.

14. The stent according to claim 13 wherein the third winding has a wave length of about 0.050.

15. The stent according to claim 13 wherein the third winding has a wave amplitude of about 0.030 inches.

16. A stent according to claim 1 where the first, second and third winding are formed from a unitary wire.

17. A method for making a stent body for implantation within a body vessel comprising the steps of:

preforming a first wire segment into an evenly expandable helical sinusoidal wave pattern wound into a continuous helix the length of the stent, the first wire segment having a proximal end and a distal end, each wave having a wave length and a wave amplitude such that the wave length and wave amplitude ratio results in unaligned wave apexes in adjoining waves;

preforming a second wire segment into an evenly expandable helical sinusoidal wave pattern, the second wire segment having a proximal end and a distal end;

preforming a third wire segment into an evenly expandable helical sinusoidal wave pattern, the third wire segment having a proximal end and a distal end;

winding the preformed first wire segment on a cylindrical mandrel such that the pattern is retained;

winding the preformed second wire segment on the mandrel such that the pattern is retained, the second wire segment having a wave length which is less than the wave length of the first wire segment such than the second wire segment has more wire per unit surface area than the first wire segment;

attaching the proximal end of the second wire segment to the distal end of the second wire segment to form a ring;

attaching the proximal end of the first wire segment to the second wire segment;

winding the preformed third wire segment on the mandrel such that the pattern is retained, the third wire segment having a wave length which is less than the wave length of the first wire segment such that the third wire segment has more wire per unit surface area than the first wire segment;

attaching the proximal end of the third wire segment to the distal end of the third wire segment to form a ring; and attaching the distal end of the first wire segment to the third wire segment.

18. The method of claim 17 further including the step of selecting a unitary wire for the first, second and third wire segments.

19. The method according to claim 17 further including the step of selecting the first, second and third wire with a sinusoidal wave form having a uniform wave length and wave amplitude.

20. The method according to claim 19 further including the step of selecting the wave amplitude of the second and third wire segments which is less than the wave amplitude of the first wire pattern.

21. A radially expandable stent for implantation within a body vessel, comprising:

a first wire formed winding having a hollow cylindrical shape defining a lumen, the first winding including a preformed sinusoidal wave pattern wound into a continuous helix the length of the stent which permits even expansion of the first winding, the first winding having a proximal end and a distal end, each wave having a wave length and a wave amplitude such that the wave length and wave amplitude ratio results in unaligned wave apexes in adjoining waves of the first wire formed winding;

a second wire formed winding having a hollow cylindrical shape defining a lumen, the second winding including a preformed sinusoidal wave pattern wound into a continuous helix which permits even expansion of the second winding, the second winding having a wave length which is less than the wave length of the first winding and a wave amplitude which is less than the wave amplitude of the first winding such that the second winding has more wire per unit surface area than the first winding, the second winding having a proximal end and a distal end attached to each other to form a ring, the second winding being attached to the proximal end of the first winding;

a third wire formed winding having a hollow cylindrical shape defining a lumen, the third winding including a preformed sinusoidal wave pattern wound into a continuous helix which permits even expansion of the third winding, the third winding having a wave length which is less than the wave length of the first winding and a wave amplitude which is less than the wave amplitude of the first winding such that the third winding has more wire per unit surface area than the first winding, the third winding having a proximal end and a distal end attached to each other to form a ring, the third winding being attached to the distal end of the first winding, each second wire formed winding wave having a wave length and a wave amplitude such that the wave length and wave amplitude ratio results in unaligned wave apexes in adjoining waves of the first wire formed winding, each third wire formed winding wave having a wave length and a wave amplitude such that the wave length and wave amplitude ratio results in unaligned wave apexes in adjoining waves of the first wire formed winding; and a means extending longitudinally throughout the first, second and third winding lumens to expand the first, second and third windings.

\* \* \* \* \*